(12) United States Patent
Tang et al.

(10) Patent No.: US 6,384,209 B1
(45) Date of Patent: May 7, 2002

(54) SULFUR TRANSFER REAGENTS FOR OLIGONUCLEOTIDE SYNTHESIS

(75) Inventors: Jin-Yan Tang; Zhaoda Zhang, both of Shrewsbury, MA (US)

(73) Assignee: Avecia Biotechnology, Inc., Blackley (GB)

( * ) Notice: Subject to any disclaimer, the term of this patent is extended or adjusted under 35 U.S.C. 154(b) by 0 days.

(21) Appl. No.: 08/979,864

(22) Filed: Nov. 26, 1997

Related U.S. Application Data

(63) Continuation of application No. 09/697,847, filed on Aug. 30, 1996, now abandoned.

(51) Int. Cl.$^7$ .............................................. C07H 21/00

(52) U.S. Cl. ................. 536/25.3; 536/25.33; 536/25.34

(58) Field of Search ............................ 536/25.3, 25.33, 536/25.34, 22

(56) References Cited

U.S. PATENT DOCUMENTS

| | | | |
|---|---|---|---|
| 3,753,908 A | 8/1973 | de Vries | |
| 3,923,763 A | * 12/1975 | Edmondson | ................. 526/217 |
| 5,502,066 A | 3/1996 | Heinemann et al. | ......... 514/360 |
| 6,114,519 A | * 9/2000 | Cole et al. | ................ 536/25.34 |

OTHER PUBLICATIONS

Zhang et al.(I), "Synthesis and Properties of Novel Thiono Triester Modified Antisense Oligodeoxynucleotide Phosphorothioates," *Bioorganic & Medicinal Chemistry Letters*, 5(15), 1735–1740(Aug. 3, 1995).*

Zhang et al. (II), "Thiono Triester Modified Antisense Oligonucleotides for Inhibition of Human Cytomegalovirus In Vitro," *Bioorganic & Medicinal Chemistry Letters*, 6(16), 1911–1916(Aug. 20, 1996).*

Bokarev et al., "Synthesis of Bis(Alkyl Xanthyl) Trisulfides," *Izv. Akad. Nauk SSR, Ser. Khim.*, 1964(12), 2175–2182; *Chemical Abstracts*, 62(7), Abstract No. 7631d (Mar. 29, 1965); only Abstract supplied.*

Scholl et al., "Novel Symmetrical and Mixed Carbamoyl and Amino Polysulfanes by Reactions of (Alkoxydichloromethyl)polysulfuranyl Substrates with N–Methylaniline," *Journal of Organic Chemistry*, 51(10), 1866–1881 (1986).*

Barany et al., "A General Strategy for Elaboration of the Dithiocarbonyl Functionality, –(C=O)SS–: Application to the Synthesis of Bis(chlorocarbonyl)disulfine and Related Derivatives of Thiocarbonic Acids," *Journal of Organic Chemistry*, 48(24), 4750–4761 (Dec. 2, 1983).*

Tittelbach, "Synthesis and Dimroth Rearrangement of Disubstituted 5–Imino–1,2,4–dithiazolidino–3–thione (Mustard Oil Sulfides)," *J. Prakt. Chem.*, 333(1), 1078–117 (1991); *Chemical Abstracts*, 115(9), p. 755, Abstract No. 92183c (Sep. 2, 1991); only abstract supplied.†\*

Tittelbach et al., "Cycloaddition–elimination Reactions of Phenyl Isocyanate with Oxo and Thiono Derivatives of Aliphatic Substituted 5–imino–1,2,4–dithiazolidines and 3–Thiono–1,2,4–thiadiazolidines (Mustard Oil Oxides and Sulfides)," *J. Prakt. Chem.*, 334(8), 685–690 (1992); *Chemical Abstracts*, 118(19), p. 947, Abstract No. 191647d (May 10, 1993); only abstract supplied.††*

Vu et al., "Internucleotide Phosphite Sulfurization with Tetraethylthiuram Disulfide. Phosphorothioate Oligonucleotide Synthesis via Phosphoramidite Chemistry," *Tetrahedron Letters*, 32(26), 3005–3008 (1991).††*

Rao et al., "Dibenzoyl Tetrasulfide—A Rapid Sulfur Transfer Agent in the Synthesis of Phosphorotioate Analogues of Oligonucleotides," *Tetrahedron Letters*, 33(33), 4839–4842 (1992).††*

Stec et al., "Bis(O,O–Diisoproxy Phosphinothioyl)Disulfide—A Highly Efficient Sulfurizing Reagent for Cost–Effective Synthesis of Oligo(Nucleoside Phosphorothioate)s," *Tetrahedron Letters*, 34(33), 5317–5320 (1993).††*

Efimov et al., "New Efficient Sulfurizing Reagents for the Preparation of Oligodeoxyribonucleotide Phosphorothioate Analogues," *Nucleic Acids Research*, 23(20), 4029–4033 (1995).††*

PCT International Preliminary Examination Report (PCT Article 36 and Rule 70) International Application No. PCT/US98/10653; Date of Completion of Report: Jul. 22, 1999 (5 pages).

PCT International Preliminary Examination Report (PCT Article 36 and Rule 70) International Application No. PCT/US98/08763; Date of Completion of Report: 30/07/99 (6 pages).

Chemical Abstracts, vol. 59, No. 6, Sep. 16, 1963, Columbus, Ohio, US; Abstract No. 6934e, M. Nagasawa et al., "Organophosphorous insecticides containing sulfonyl radicals" and JP 62 015 649 A (Ihara Agricultural Chemical Co.) Oct. 1, 1960.

(List continued on next page.)

*Primary Examiner*—James O. Wilson
*Assistant Examiner*—L. Eric Crane
(74) *Attorney, Agent, or Firm*—Hamilton, Brook, Smith & Reynolds, P.C.

(57) ABSTRACT

The invention relates to the chemical synthesis of oligonucleotides and to chemical entities useful in such synthesis. More particularly, the invention relates to sulfurization of the internucleoside linkages of oligonucleotides. The invention provides new sulfur transfer reagents and processes for their use in sulfurizing oligonucleotides. The sulfur transfer reagents according to the invention are inexpensive to make, stable in storage and highly efficient in sulfurization.

7 Claims, 3 Drawing Sheets

OTHER PUBLICATIONS

Chemical Abstracts, vol. 85, No. 25, Dec. 20, 1976, Columbus, Ohio, US; Abstract No. 187433p, T. Chiyonishio, "Effect of nematicides on the occurrence of black and scurf of Chinese yam in sand dune fields", p. 112; Col. 1 and Tottori–Ken Nogyo Shikenjo Kenkyu Hokoku, vol. 13, 1973, pp. 29–52.

Chemical Abstracts, vol. 58, No. 10, May 13, 1963, Columbus, Ohio, US; Abstract No. 10125e, F. Cano et al., "S–Alkyl and arylsulfonyalkyl dithiophosphates" and IT 605 426 A (S.A.R.I.F.) May 27, 1960.

Chemical Abstracts, vol. 68, No. 7, Feb. 12, 1968, Columbus, Ohio, US; Abstract No. 28718t, T. Saito et al., "Systemic insecticidal properties of certain organic phosporus compounds to the green peach aphid, *Myzus persicae*, and the tobacco cutworm, *Prodenis litura*", p. 2767, Col. 1 and Bochu Kaguku, vol. 31, No. 2, 1966, pp. 77–81.

Nucleic Acids Research, vol. 24, No. 9, May 1, 1996, XU Q et al., "Use of 1,2,4–dithiazolidine–3,5,–dione (DtsNH) and 3–ethoxy–1,2,4–dithiazoline–5–one (Edith) for synthesis of phosphorothioate–containing oligodeoxyribonucleotides", pp. 1602–1607.

Nucleic Acids Research, vol. 24, No. 18, Sep. 15, 1996, Xu Q et al., "Efficient introduction of phosphorothioates into RNA oligonucleotides by 3–ethoxy–1,2, 4–dithiazoline–5–one (Edith)", pp. 3643–3644.

Journal of Organic Chemistry, vol. 55, No. 15, Jul. 20, 1990, Iyer, R.P. et al., "The Automated synthesis of sulfur–containing oligodeoxyribonucleotides Using 3H–1,2–Benzodithiol–3–one 1,1,–Dioxide as a Sulfur–Transfer Reagent", pp. 4693–4699.

* cited by examiner (A)

(B)

| Sulfurizing Reagents | Concentration (M) | Molar Equivalent | Solvent | Reaction Time (min) | P=O (%) | P=S (%) |
|---|---|---|---|---|---|---|
| Beaucage | 0.06 | 11 | CH$_3$CN | 1 | 0.68 | 99.32 |
|  |  |  |  | 5 | 0.92 | 99.08 |
| TETD | 0.5 | 90 | CH$_3$CN | 1 | 4.55 | 95.45 |
|  |  |  |  | 5 | 3.00 | 97.00 |
| Reese | 0.4 | 72 | THF | 1 | 4.42 | 95.58 |
|  |  |  |  | 5 | 2.21 | 97.79 |
| Stec | 0.2 | 37 | Pyridine | 1 | 1.55 | 98.45 |
|  |  |  |  | 4 | 0.71 | 99.29 |
|  | Saturated | 37 | CH$_3$CN | 1 | 9.49 | 90.51 |
|  |  |  |  | 5 | 8.18 | 91.82 |
| Efimov | 0.2 | 37 | DCM:Py(9:1) | 1 | 2.07 | 97.93 |
| Barany | 0.02 | 4 | CH$_3$CN | 1 | 0.41 | 99.59 |
|  |  |  |  | 4 | 0.6 | 99.40 |
| 1-A | 0.08 | 15 | Pyridine | 1 | 0.63 | 99.37 |
|  |  | 10 | Pyridine | 5 | 0.31 | 99.69 |
|  | 0.16 | 30 | THF:Py (9:1) | 2 | 0.43 | 99.57 |

FIG. 3

SULFUR TRANSFER REAGENTS FOR OLIGONUCLEOTIDE SYNTHESIS

This application is a of continuation application Ser. No. 08/697,847, filed Aug. 30, 1996, now abandoned.

BACKGROUND OF THE INVENTION

1. Field of the Invention

The invention relates to the chemical synthesis of oligonucleotides and to chemical entities useful in such synthesis. More particularly, the invention relates to sulfurization of the internucleoside linkages of oligonucleotides.

2. Summary of the Related Art

Oligonucleotides have become indispensible tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides.

The synthesis of oligonucleotides for antisense and diagnostic applications can now be routinely accomplished. See e.g., *Methods in Molecular Biology*, Vol 20: *Protocols for Oligonucleotides and Analogs* pp. 165–189 (S. Agrawal, Ed., Humana Press, 1993); *Oligonucleotides and Analogues: A Practical Approach*, pp. 87–108 (F. Eckstein, Ed., 1991); and Uhlmann and Peyman, supra. Agrawal and Iyer, *Curr. Op. in Biotech.* 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., *J. Molec. Biol.* 72: 209 (1972) discloses phosphodiester chemistry for oligonucleotide synthesis. Reese, *Tetrahedron Lett.* 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28: 3539–3542 (1987), teaches synthesis of oligonucleotide methylphosphonates using phosphoramidite chemistry. Connolly et al., *Biochemistry* 23: 3443 (1984), discloses synthesis of oligonucleotide phosphorothioates using phosphoramidite chemistry. Jager el al., *Biochemistry* 27: 7237 (1988), discloses synthesis of oligonucleotide phosphoramidates using phosphoramidite chemistry. Agrawal et al., *Proc. Natl. Acad. Sci. USA* 85: 7079–7083 (1988), discloses synthesis of oligonucleotide phosphoramidates and phosphorothioates using H-phosphonate chemistry.

Solid phase synthesis of oligonucleotides by each of the foregoing processes involves the same generalized protocol. Briefly, this approach comprises anchoring the 3'-most nucleoside to a solid support functionalized with amino and/or hydroxyl moieties and subsequently adding the additional nucleosides in stepwise fashion. Internucleoside linkages are formed between the 3' functional group of the incoming nucleoside and the 5' hydroxyl group of the 5'-most nucleoside of the nascent, support-bound oligonucleotide. In the phosphoramidite approach, the internucleoside linkage is a phosphite linkage, whereas in the H-phosphonate approach, it is an H-phosphonate internucleoside linkage. To create the sulfur-containing phosphorothioate internucleoside linkage, the phosphite or H-phosphonate linkage must be oxidized by an appropriate sulfur transfer reagent. In the H-phosphonate approach, this sulfurization is carried out on all of the H-phosphonate linkages in a single step following the completion of oligonucleotide chain assembly, typically using elemental sulfur in a mixed solvent such as $CS_2$/pyridine. In contrast, the phosphoramidite approach allows stepwise sulfurization to take place after each coupling, thereby providing the capability to control the state of each linkage in a site-specific manner.

Refinement of methodologies is still required, however, particularly when making a transition to large-scale synthesis ($10 \mu mol$ to 1 mmol and higher). See Padmapriya et al., *Antisense Res. Dev.* 4: 185 (1994). Several modifications of the standard phosphoramidite processes have is already been reported to facilitate the synthesis (Padmapriya et al., supra; Ravikumar et al., *Tetrahedron* 50: 9255 (1994); Theisen et al., *Nucleosides & Nucleotides* 12: 43 (1994); and Iyer et al., *Nucleosides & Nucleotides* 14: 1349 (1995)) and isolation (Kuijpers et al. Nucl. Acids Res. 18: 5197 (1990); and Reddy et al., *Tetrahedron Lett.* 35: 4311 (1994)) of oligonucleotides.

In the case of sulfurization, the need for refinement is manifest. Elemental sulfur is not an efficient sulfur transfer reagent due to its poor solubility and slow sulfurization reaction. Consequently, numerous efforts have been made to discover improved sulfur transfer reagents. Kamer et al., *Tetrahedron Lett.* 30: 6757–6760 (1989) teaches the use of phenylacetyl disulfide as a sulfur transfer reagent. Iyer et al., *J. Org. Chem.* 55: 4693–4699 (1990) discloses DNA sulfurization using 3H-1,2-benzodithiol-3-one-1,1-dioxide (Beaucage reagent). Vu et al., *Tetrahedron Lett.* 32: 3005–3008 (1991) teaches sulfur transfer using tetraethylthiuram disulfide (TETD). Rao et al., *Tetrahedron Lett.* 33: 4839–4842 (1992) discloses dibenzoyl tetrasulfide as a sulfurizing agent. Stec et al., *Tetrahedron Lett.* 33: 5317–5320 (1993) teaches DNA sulfurization using bis(O,O,-diisopropoxyphosphinothioyl) disulfide (S-Tetra). Rao et al., *Tetrahedron Lett.* 35: 6741–6744 (1994) discloses benzyltriethyl-ammonium tetrathiomolybate (BTTM) as a sulfur transfer reagent. Effimov et al., Nucleic Acids Res. 23: 4029–4033 (1995) teaches the use of bis(p-toluenesulfonyl) disulfide for sulfur transfer. Xu et al., discloses 3-ethoxy-1, 2,4-dithiazoline-5-one (EDITH) and 1,2,4-dithiazolidine-3, 5-dione (DTSNH) as sulfur transfer reagents. Unfortunately, each of these reagents has its limitations and only Beaucage reagent and TETD have become commercially available, with only Beaucage reagent being widely used. Moreover, Beaucage reagent has sub-optimal synthesis and stability characteristics and during sulfurization forms a by-product, 3H-2,1-benzoxathiolan-3-one-1-oxide, which is a powerful oxidizing agent capable of producing unwanted phosphodiester internucleoside linkages.

There is, therefore, a need for new sulfur transfer reagents and processes for sulfurizing oligonucleotides. Ideally, such reagents should be inexpensive to make, stable in storage and highly efficient in sulfurization.

BRIEF SUMMARY OF THE INVENTION

The invention provides new sulfur transfer reagents and processes for their use in sulfurizing oligonucleotides. The sulfur transfer reagents according to the invention are inexpensive to make, stable in storage and highly efficient in sulfurization.

In a first aspect, the invention provides novel sulfur transfer reagents having the general structure:

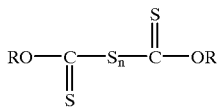

wherein each R is independently a lower alkyl group containing 1–6 saturated or unsaturated carbon atoms, or an aryl or allyl group having 2–6 carbon atoms, wherein such alkyl, aryl or allyl group may be unsubstituted or may be substituted, e.g., with halogen, hydroxy, trifluoromethyl, cyano, nitro, acyl, acyloxy, alkoxy, carboxy, carbalkoxy, or amino groups. In a particularly preferred embodiment, each R is an ethyl group.

In a second aspect, the invention provides novel processes for adding a sulfur group to an internucleoside linkage of an oligonucleotide using the novel sulfur transfer reagents according to the invention. In preferred embodiments, the novel processes according to the invention comprise contacting an oligonucleotide having at least one sulfurizable internucleoside linkage with a novel sulfur transfer reagent according to the invention for a time sufficient for sulfurization of the sulfurizable internucleoside linkage(s) to occur.

BRIEF DESCRIPTION OF THE DRAWINGS

FIG. 3 shows comparative results for sulfur transfer using prior art sulfur tranfer reagents or novel sulfur transfer reagents according to the invention.

DETAILED DESCRIPTION OF THE PREFERRED EMBODIMENTS

The invention relates to the chemical synthesis of oligonucleotides and to chemical entities useful in such synthesis. More particularly, the invention relates to sulfurization of the internucleoside linkages of oligonucleotides. The patents and publications identified in this specification are within the knowledge of those skilled in this field and are hereby incorporated by reference in their entirety.

The invention provides new sulfur transfer reagents and processes for their use in sulfurizing oligonucleotides. The sulfur transfer reagents according to the invention are inexpensive to make, stable in storage and highly efficient in sulfurization.

In a first aspect, the invention provides novel sulfur transfer reagents having the general structure:

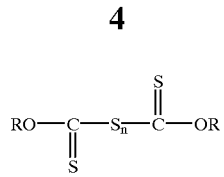

wherein n is 3 or 4 and each R is independently a lower alkyl group containing 1–6 saturated or unsaturated carbon atoms, or an aryl or allyl group having 2–6 carbon atoms, wherein such alkyl, aryl or allyl group may be unsubstituted or may be substituted, e.g., with halogen, hydroxy, trifluoromethyl, cyano, nitro, acyl, acyloxy, alkoxy, carboxy, carbalkoxy, or amino groups. In a particularly preferred embodiment, each R is an ethyl group.

Figure 1:
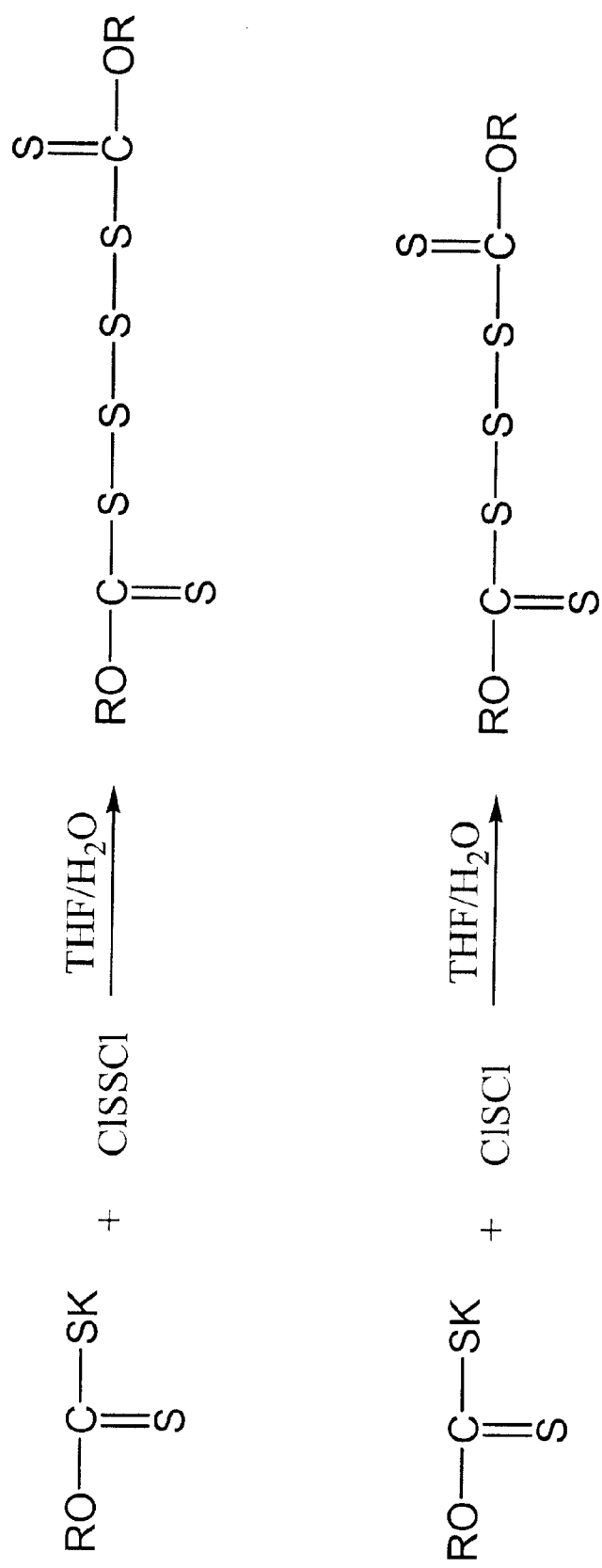
FIG. 1 shows a scheme for synthesis of novel sulfur transfer reagents according to the invention.

The novel sulfur transfer reagents according to the invention are conveniently prepared according to the scheme shown in FIG. 1. Briefly, the novel sulfur transfer reagents can easily be prepared from the corresponding alkali metal alkyl, aryl or allyl xanthogenate in an appropriate solvent in the presence of an appropriate sulfur halide. Preferred alkyl, aryl and allyl xanthogenates include potassium ethylxanthogenate. Preferred solvents include mixtures of THF and $H_2O$. Preferred sulfur halides include sulfur monochloride and sulfur dichloride. The desired product can be obtained by extraction with dichloromethane, followed by washing of the organic phase with dilute sodium carbonate, then with saturated sodium chloride, followed by drying, filtration and solvent removal. The novel sulfur transfer reagents can thus be obtained at high yield in a single step without the need for chromatographic separation. The starting materials are readily available and inexpensive and the novel sulfur transfer reagent is stable at room temperature.

In a second aspect, the invention provides novel processes for adding a sulfur group to an internucleoside linkage of an oligonucleotide using the novel sulfur transfer reagents according to the invention. In preferred embodiments, the novel processes according to the invention comprise contacting an oligonucleotide having at least one sulfurizable internucleoside linkage with a novel sulfur transfer reagent according to the invention for a time sufficient for sulfurization of the sulfurizable internucleoside linkage(s) to occur. Each sulfurizable internucleoside linkage preferably contains a phosphorous (III) atom. In a particularly preferred embodiment, the sulfurizable internucleoside linkage is a phosphite, thiophosphite, H-phosphonate, thio-H-phosphonate, or alkylphosphite (especially methylphosphite) internucleoside linkage. Preferably, the sulfurization reaction is allowed to proceed to a sulfur transfer efficiency of >99%, as measured by $^{31}$P-NMR. In typical synthesis conditions such efficiency is achieved within from about 1 to about 5 minutes reaction time with the novel transfer reagents.

Typically, the reaction takes place in pyridine, THF, or mixtures thereof. For purposes of this aspect of the invention, the term oligonucleotide includes polymers of two or more deoxyribonucleotide, ribonucleotide, or 2'-O-substituted ribonucleotide monomers, or any combination thereof. The term oligonucleotide also encompasses such polymers having chemically modified bases or sugars and/or having additional substituents, including without limitation lipophilic groups, intercalating agents, diamines and adamantane. For purposes of the invention the term "2'-O- substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halogen, hydroxy, trifluoromethyl, cyano, nitro, acyl, acyloxy, alkoxy, carboxy, carbalkoxy, or amino groups; or with a hydroxy, an amino or a halogen group, but not with a 2'-H group. Such oligonucleotides may include any of the internucleoside linkages which are known in the art, including without limitation phosphorothioate, phosphorodithioate, alkylphosphonate (especially methylphosphonate), phosphoramidate, amide (PNA), carbamate, and alkylphosphonothioate linkages. In a preferred embodiment, the oligonucleotide is bound to a solid support, but such oligonucleotides may be sulfurized in solution phase as well.

The following examples are intended to further illustrate certain preferred embodiments of the invention and are not intended to be limiting in nature. Except as otherwise stated herein, anhydrous pyridine, tetrahydrofuran and dichloromethane were purchased from Aldrich (Milwaukee, Wis.). Anhydrous acetonitrile was purchased from J. T. Baker inc. (Phillipsburg, N.J.). dT-CPG, 5'-DMT-deoxyadenosine (Bz) cyanoethyl phosphoramidite, 5'-DMT-deoxycytidine (Bz) cyanoethyl phosphoramidite, 5'-DMT-deoxyguanosine (ibu) Cyanoethyl phosphoramidite, 5'-DMT-thymidine Cyanoethyl phosphoramidite, Cap A, Cap B, activator, oxidizing and deblock solutions were purchased from PerSeptive Biosystems (Framingham, Mass.). Beaucage reagent ($^3$H-1,2-benzodithiol-3-one-1,1-dioxide) was purchased from R. I. Chemical (Orange, Calif.). All other chemicals were purchased from Aldrich. $^{31}$P NMR spectra (121.65 MHz) and $^1$H NMR spectra (300 MHz) were recorded on a Varian UNITY 300 (the chemical shift was correlated to 85% H$_3$PO$_4$ and tetramethylsilane, respectively). Dinucleotide and oligonucleotide synthesis was performed on an automated nucleic acid synthesizer (8909 Expedite™, Millipore, Bedford, Mass.). Reverse phase HPLC was performed on a Waters 600E with a Waters 440 absorbance detector, Waters 746 integrator and a Waters Nova-Pak Radial-Pak C18 (8×100 mm) column at flow rate of 2 mL/min. Eluents were (A) 100 mM ammonium acetate and (B) 80% acetonitrile/20% 100 mM ammonium acetate. Starting at 90% A, the gradient was: 10 to 60% B in 40 min; to 100% B in 5 min; to 0% B in 5 min. Ion-exchange HPLC was performed on a Beckman System Gold 126 with a Beckman 166 absorbance detector, Beckman 507 autosampler and NUCLEO PAC™ PA-100 GUARD column (Dionex Corporation, Sunnyvale, Calif.) at flow rate of 2 mL/min. Eluents were (A) 25 mM Tris, 1 mM EDTA, 10% CH$_3$CN, pH8 and (B) 2.5 M ammonium chloride, 25 mM Tris, 1 mM EDTA, 10% CH3CN, pH8. Starting at 0% B, the gradient was: 0–100% B in 5 min, maintained 100% B for 2 min, 100%–0% B in 0.5 min. Capillary electrophoresis was performed on a Beckman P/ACE System 5010. Samples were injected for 5 seconds and analyzed for 40 min.

EXAMPLE 1
Synthesis of Bis(Ethoxythiocarbonyl)Tetrasulfide (1-A).
To a solution of potassium ethylxanthogenate (40 g., 0.25 mol) in THF (100 mL) and H$_2$O (100 mL) was added dropwise sulfur monochloride (33.76 g., 20 mL, 0.25 mol) at 0° C. The reaction mixture was stirred at room temperature overnight, and extracted with 300 mL of CH$_2$Cl$_2$. The organic phase was washed with 5% Na$_2$CO$_3$ solution followed by saturated NaCl solution, and dried over anhydrous potassium sulfate for 3 h. The solution was filtered, and the solvent was removed at reduced pressure to give the product as a pale yellow oil (29.6 g., 96.6 mmol, 77.3%): $^1$H NMR (CDCl$_3$) δ4.68 (m, 4H), 1.45 (m, 6H).

EXAMPLE 2
Synthesis of Bis(Ethoxythiocarbonyl)Trisulfide(1-B)
To a solution of potassium ethylxanthogenate (8 g., 0.25 mol) in THF (50 mL) and H$_2$O (50 mL) was added 1M solution of sulfur dichloride in CH2Cl2(25 mL, 0.025 mol) at the room temperature. The reaction mixture was stirred at room temperature overnight, and extracted with 100 mL of CH$_2$Cl$_2$. The organic phase was washed with 5% Na$_2$CO$_3$ solution followed by saturated NaCl solution, and dried over anhydrous potassium sulfate for 3 h. The solution was filtered, and the solvent was removed at reduced pressure to give the product as a pale yellow oil (3.2 g, 11.5 mmol, 46%):$^1$H NMR (CDCl$_3$) δ 4.66 (m, 4H), 1.45 (m, 6H).

Figure 2:
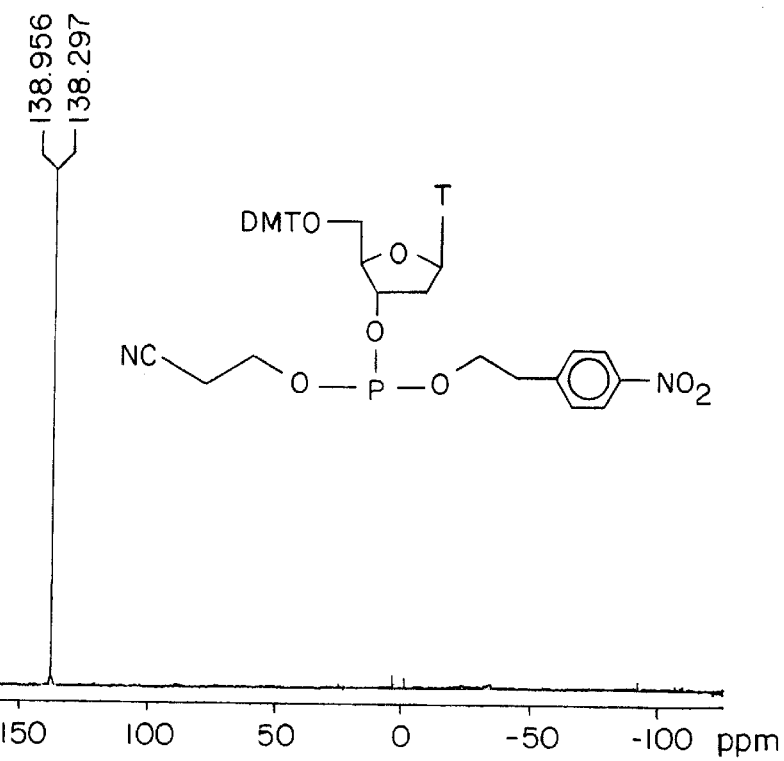
FIG. 2 shows $^{31}$P-NMR results for sulfurization of a nucleoside phosphite using a novel sulfur tranfer reagent according to the invention.
Figure 2:
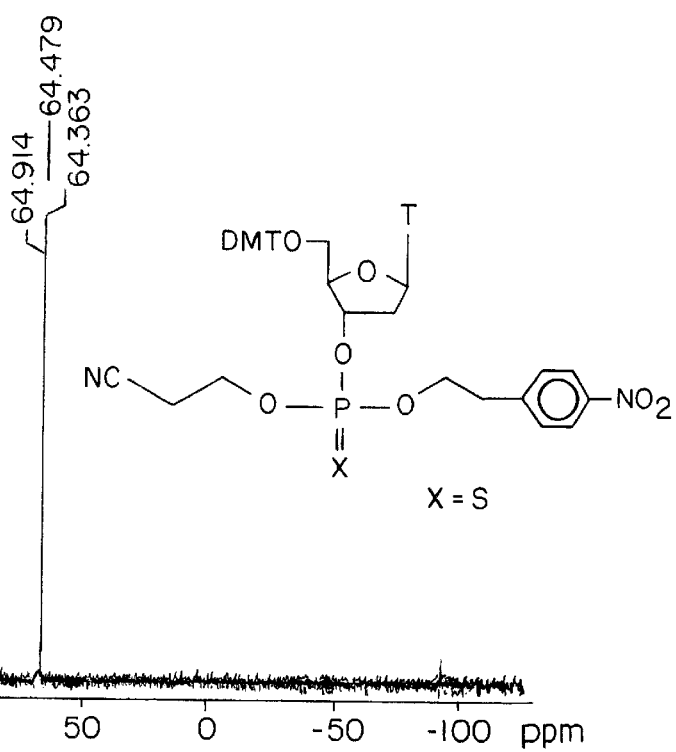

EXAMPLE 3
Analysis of Sulfur-Transfer Reagents Using 31P NMR Spectroscopy.
To 0.10 mmol of 1-A (30.6 mg) in CDCl$_3$ (0.5 mL) was added a solution of 5'-O-dimethoxytritylthymidine-3'-O-(2-cyanoethyl) 4-nitrophenyl phosphite (40 mg, 0.05 mmol) in CDCl$_3$ (0.5 mL) at room temperature. After stirring for 0.5 min. at room temperature, the solution was transferred into a NMR tube and examined by a NMR spectrometer. The results are shown in FIG. 2. These results demonstrate that the sulfurised phosphite is obtained as a single species.

EXAMPLE 4
Synthesis and Sulfurization of Dimer and Oligomers
Dinucleotide and oligonucleotide phosphorothioates were synthesized on 1 μmol scale using an automated synthesizer (Millipore 8909 Expedites™, Millipore, Bedford, Mass.). Before use, solutions of the sulfurizing reagents were placed over activated 4 A molecular sieves overnight. The synthesis protocol "THIO 1 μmol" (Expedite™ software version 1.01) was used with the following modifications: 1. Capping was performed after the sulfurization step; 2. Delivery time of sulfurization reagents and acetonitrile wash step following sulfurization was extended in some cases as indicated. Two-hour treatment with ammonium hydroxide at room temperature was carried out to cleave the dimer-from the support. Eight-hour treatment with ammonium hydroxide at 55° C. was carried out to cleave the oligomer from the support and to deprotect nucleoside bases. The mixture was filtered to remove the CPG. After removal of the ammonium hydroxide solution, the remaining crude products were submitted for CE, ion-exchange HPLC and NM analysis.

Comparative results for the sulfur transfer reagents according to the invention and various prior art reagents are shown in FIG. 3. These results demonstrate the superior efficiency of the novel sulfur transfer reagents according to the invention.

What is claimed is:
1. A process for adding a sulfur group to an internucleoside phosphorous (III) linkage of an oligonucleotide, the process comprising contacting an oligonucleotide having at least one internucleoside linkage comprising a phosphorous (III) atom with a sulfur transfer reagent having the general structure:

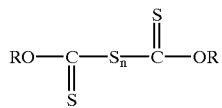

wherein:
  n is 3 or 4;
  each R is independently a lower alkyl group containing 1–6 saturated or unsaturated carbon atoms, an aryl, or an allyl group having 2–6 carbon atoms, wherein the alkyl, aryl or allyl group may be unsubstituted or may be substituted with a substituent selected from the group consisting of halogen, hydroxy, trifluoromethyl, cyano, nitro, acyl, acyloxy, alkoxy, carboxy, carbalkoxy, or amino for a time sufficient for sulfurization of the internucleoside linkage(s) to occur.

2. The process according to claim 1, wherein the sulfurizable internucleoside linkage is a phosphite, thiophosphite, H-phosphonate, thio-H-phosphonate, or alkylphosphite internucleoside linkage.

3. The process according to claim 1, wherein the sulfurization reaction is allowed to proceed to a sulfur transfer efficiency of >99%, as measured by $^{31}$P-NMR.

4. The process according to claim 1, wherein the sulfurization reaction is allowed to proceed from about 1 to about 5 minutes.

5. A process according to claim 1, wherein each R is an ethyl group.

6. A process according to claim 1, wherein n is 4.

7. A process according to claim 1, wherein n is 3.

* * * * *

UNITED STATES PATENT AND TRADEMARK OFFICE
CERTIFICATE OF CORRECTION

PATENT NO. : 6,384,209 B1
DATED : May 7, 2002
INVENTOR(S) : Jin-Yan Tang and Zhaoda Zhang It is certified that error appears in the above-identified patent and that said Letters Patent is hereby corrected as shown below:

<u>Title page,</u>
Item [63], please delete "09/697,847" and insert therefor -- 08/697,847 --.

Signed and Sealed this

Tenth Day of September, 2002

Attest:

JAMES E. ROGAN
Attesting Officer     Director of the United States Patent and Trademark Office